(12) United States Patent
Valdes et al.

(10) Patent No.: US 8,211,281 B2
(45) Date of Patent: Jul. 3, 2012

(54) CATALYST ANNEAL FOR DURABLE STOICHIOMETRIC SHIFT CORRECTED PROTECTIVE COATING FOR OXYGEN SENSORS

(75) Inventors: Carlos A. Valdes, Flint, MI (US); Marsha Nottingham, Howell, MI (US); Earl W. Lankheet, Grand Blanc, MI (US); Eric P. Clyde, Bay City, MI (US)

(73) Assignee: Delphi Technologies, Inc., Troy, MI (US)

( * ) Notice: Subject to any disclaimer, the term of this patent is extended or adjusted under 35 U.S.C. 154(b) by 524 days.

(21) Appl. No.: 11/870,206

(22) Filed: Oct. 10, 2007

(65) Prior Publication Data

US 2008/0135407 A1 Jun. 12, 2008

Related U.S. Application Data

(60) Provisional application No. 60/828,946, filed on Oct. 10, 2006.

(51) Int. Cl.
*G01N 27/407* (2006.01)

(52) U.S. Cl. .................. 204/429; 204/424; 427/98.3

(58) Field of Classification Search .................. 204/400, 204/424, 428, 429; 73/19.01, 23.2–31.07; 60/274–293; 427/98.3
See application file for complete search history.

(56) References Cited

U.S. PATENT DOCUMENTS

| | | | | |
|---|---|---|---|---|
| 4,878,473 | A * | 11/1989 | Nakaniwa et al. | 123/691 |
| 6,555,159 | B2 * | 4/2003 | Clyde et al. | 427/126.3 |
| 7,097,875 | B2 * | 8/2006 | Clyde et al. | 427/115 |
| 2002/0008025 | A1 * | 1/2002 | Fujii et al. | 204/429 |

* cited by examiner

*Primary Examiner* — Kaj K Olsen
*Assistant Examiner* — Susan D Leong
(74) *Attorney, Agent, or Firm* — Mark H. Svoboda

(57) ABSTRACT

In one embodiment, a protective coating for an electrode of a sensor is described, the protective coating comprising an annealed catalyst, said annealed catalyst comprising at least one metal that has been subjected to thermal energy that is at least equivalent to or greater than that received from calcining the at least one metal for 24 hours at a temperature of 930 degrees C in air. In another embodiment, the annealed catalyst will comprise at least one metal that has been subjected to thermal energy that is equal to or less than that received from calcining the at least one metal for 24 hours at 1030 degrees C in air. In one exemplary embodiment, the annealed catalyst will comprise at least one metal that has been subjected to thermal energy that is equal to that received from calcining the at least one metal for 24 hours at 980 degrees C in air.

9 Claims, 12 Drawing Sheets

| HOURS ON SILOXANE TEST | | | | | 0 | | | | | | | | 30 | |
|---|---|---|---|---|---|---|---|---|---|---|---|---|---|---|
| DESCRIPT | PLATINUM | U-COAT TH | O-COAT TH | TEMP | VMin | VMax | LRTime | RLTime | RESIST | SLamRLBch | SLamLRBch | AvLambda | VMin | VMax |
| 1 | 0 | STD | STD | REF | 88 | 788 | 12 | 50 | 1569.4 | 1.003 | 1.0028 | 1.0029 | 88 | 793 |
| 2 | 0.25 | 100 | 50 | 930 | 78 | 775 | 19 | 40 | 1711 | 1.0008 | 1.0004 | 1.0006 | 75 | 779 |
| 3 | 0.35 | 100 | 50 | 930 | 79 | 784 | 27 | 51 | 1645.8 | 1.0009 | 1.0005 | 1.0007 | 79 | 766 |
| 4 | 0.25 | 250 | 50 | 930 | 80 | 769 | 35 | 75 | 1459.8 | 1.0007 | 1.0002 | 1.00045 | 79 | 785 |
| 5 | 0.35 | 250 | 50 | 930 | 80 | 779 | 29 | 55 | 1645.8 | 1.0007 | 1.0003 | 1.0005 | 81 | 762 |
| 6 | 0.25 | 100 | 100 | 930 | 80 | 765 | 23 | 47 | 1664 | 1.0008 | 1.0004 | 1.0006 | 81 | 756 |
| 7 | 0.35 | 100 | 100 | 930 | 74 | 789 | 26 | 48 | 1953.5 | 1.0009 | 1.0005 | 1.0007 | 72 | 773 |
| 8 | 0.25 | 250 | 100 | 930 | 77 | 781 | 26 | 55 | 1712.2 | 1.0009 | 1.0007 | 1.0008 | 79 | 762 |
| 9 | 0.35 | 250 | 100 | 930 | 81 | 770 | 42 | 74 | 1911 | 1.0006 | 1.0002 | 1.0004 | 80 | 772 |
| 10 | 0.25 | 100 | 50 | 1030 | 78 | 761 | 24 | 49 | 1730.1 | 1.001 | 1.0005 | 1.00075 | 76 | 769 |
| 11 | 0.35 | 100 | 50 | 1030 | 75 | 757 | 23 | 48 | 2057.5 | 1.0009 | 1.0005 | 1.0007 | 73 | 782 |
| 12 | 0.25 | 250 | 50 | 1030 | 78 | 766 | 27 | 55 | 11798.5 | 1.0008 | 1.0005 | 1.00065 | 77 | 772 |
| 13 | 0.35 | 250 | 50 | 1030 | 78 | 763 | 25 | 48 | 1792 | 1.0007 | 1.0003 | 1.0005 | 80 | 756 |
| 14 | 0.25 | 100 | 100 | 1030 | 81 | 755 | 29 | 54 | 1792 | 1.0007 | 1.0002 | 1.00045 | 81 | 772 |
| 15 | 0.35 | 100 | 100 | 1030 | 73 | 770 | 24 | 45 | 1780.9 | 1.0009 | 1.0006 | 1.00075 | 74 | 782 |
| 16 | 0.25 | 250 | 100 | 1030 | 81 | 760 | 27 | 52 | 1723.7 | 1.0007 | 1.0003 | 1.0005 | 81 | 781 |
| 17 | 0.35 | 250 | 100 | 1030 | 80 | 760 | 23 | 50 | 1934.9 | 1.0009 | 1.0007 | 1.0008 | 81 | 758 |
| 18 | 0.3 | 175 | 75 | 980 | 78 | 760 | 26 | 59 | 1800.9 | 1.0007 | 1.0002 | 1.00045 | 77 | 757 |
| 19 | 0.3 | 175 | 75 | 980 | 82 | 746 | 39 | 79 | 1874.8 | 1.0006 | 1.0002 | 1.0004 | 80 | 755 |

FIG. 5A

| | | | | 30 | | | | | | | | 60 | | |
|---|---|---|---|---|---|---|---|---|---|---|---|---|---|---|
| LRTime | RLTime | RESIST | SLamRLBch | SLamLRBch | AvLambda | VMin | VMax | LRTime | RLTime | RESIST | SLamRLBch | SLamLRBch | AvLambda |
| 11 | 50 | 1756 | 1.0028 | 1.0023 | 1.00255 | 88 | 786 | 10 | 52 | 1759.3 | 1.0028 | 1.0036 | 1.0032 |
| 27 | 64 | 2034.6 | 1.0007 | 1.0015 | 1.0011 | 73 | 779 | 23 | 52 | 2093.8 | 1.0015 | 1.0022 | 1.00185 |
| 24 | 51 | 1975.3 | 1.0004 | 1.0006 | 1.0005 | 78 | 766 | 23 | 46 | 1911 | 1.0013 | 1.0017 | 1.0015 |
| 25 | 59 | 1944 | 1.0004 | 1.0014 | 1.0009 | 75 | 784 | 25 | 57 | 1944 | 1.0014 | 1.002 | 1.0017 |
| 27 | 49 | 2037.1 | 1.0002 | 0.9997 | 0.99995 | 81 | 757 | 26 | 54 | 2037.1 | 1.0013 | 1.0018 | 1.00156 |
| 25 | 49 | 1985.1 | 1.0002 | 0.9993 | 0.99975 | 81 | 752 | 24 | 51 | 1985.1 | 1.0013 | 1.0018 | 1.00155 |
| 23 | 51 | 1911 | 1.0023 | 1.00019 | 1.00065 | 72 | 763 | 22 | 45 | 1913.4 | 1.002 | 1.0026 | 1.0023 |
| 25 | 51 | 2117.3 | 1.0005 | 1.0008 | 1.00065 | 78 | 759 | 25 | 55 | 2052.3 | 1.0014 | 1.002 | 1.0017 |
| 24 | 50 | 1963.1 | 1.0003 | 0.9999 | 1.0001 | 81 | 766 | 24 | 54 | 1960.7 | 1.0014 | 1.002 | 1.0017 |
| 26 | 55 | 1594.4 | 1.0002 | 0.9992 | 0.9997 | 76 | 765 | 27 | 57 | 1592.5 | 1.0013 | 1.0018 | 1.00155 |
| 23 | 50 | 2200 | 1.0005 | 1.0013 | 1.0009 | 70 | 778 | 23 | 52 | 2217.2 | 1.0014 | 1.0021 | 1.00175 |
| 26 | 47 | 1980.2 | 1.0002 | 0.9994 | 0.9998 | 78 | 772 | 25 | 53 | 1913.4 | 1.0016 | 1.0023 | 1.00195 |
| 24 | 48 | 2174.3 | 0.9999 | 0.999 | 0.9994 | 81 | 753 | 24 | 52 | 2174.3 | 1.0012 | 1.0015 | 1.00135 |
| 28 | 64 | 1828.9 | 1.0003 | 1 | 1.00015 | 80 | 773 | 28 | 63 | 1828.9 | 1.0013 | 1.0019 | 1.0016 |
| 20 | 48 | 1965.5 | 1.001 | 1.0014 | 1.0012 | 73 | 778 | 19 | 44 | 1899.3 | 1.0015 | 1.0022 | 1.00185 |
| 25 | 57 | 1787.5 | 1.0006 | 1.0012 | 1.0019 | 81 | 755 | 24 | 50 | 1787.5 | 1.0014 | 1.0019 | 1.00165 |
| 24 | 50 | 2052.3 | 1.002 | 1.0016 | 1.0019 | 81 | 753 | 23 | 50 | 1987.5 | 1.002 | 1.0025 | 1.00225 |
| 24 | 54 | 2261.9 | 1.0009 | 1.0012 | 1.00105 | 78 | 756 | 23 | 50 | 2259 | 1.0015 | 1.002 | 1.00175 |
| 30 | 62 | 1930.1 | 1.0002 | 0.9993 | 0.99975 | 78 | 751 | 30 | 65 | 1927.7 | 1.0012 | 1.0006 | 1.0009 |

FIG. 5 B

SENSOR PERFORMANCE BEFORE AND AFTER SILOXANE AGING

| SENSOR NO. | 0 HOURS OF SILOXANE AGING | | | | | | 90 HOURS OF SILOXANE AGING | | | | | |
|---|---|---|---|---|---|---|---|---|---|---|---|---|
| | VMin | VMax | LRTime | RLTime | RESIST | Lambda | VMin | VMax | LRTime | RLTime | RESIST | Lambda |
| REFERENCE | 91 | 800 | 11 | 50 | 1752.9 | 1.0044 | 91 | 788 | 12 | 59 | 1633.8 | 1.00415 |
| 1 | 80 | 728 | 45 | 41 | 2562.2 | 1.003 | 80 | 736 | 43 | 53 | 2683.8 | 1.00305 |
| 2 | 83 | 729 | 46 | 45 | 2430.7 | 1.00155 | 81 | 741 | 45 | 55 | 2270.5 | 1.0019 |
| 3 | 86 | 738 | 47 | 48 | 2348.5 | 1.00165 | 81 | 738 | 49 | 65 | 2339.6 | 1.002 |
| 4 | 85 | 738 | 40 | 42 | 2284.9 | 1.00275 | 85 | 729 | 48 | 57 | 2348.5 | 1.00305 |
| 5 | 85 | 729 | 49 | 48 | 2360.5 | 1.00145 | 83 | 729 | 51 | 56 | 2418.3 | 1.00305 |
| 6 | 81 | 733 | 45 | 41 | 2351.5 | 1.0019 | 75 | 743 | 42 | 53 | 2342.6 | 1.0031 |
| 7 | 86 | 722 | 48 | 45 | 2701.1 | 1.0018 | 82 | 737 | 46 | 55 | 2333.7 | 1.0028 |
| 8 | 85 | 737 | 48 | 53 | 2348.5 | 1.0018 | 88 | 725 | 56 | 75 | 2348.5 | 1.0009 |
| 9 | 82 | 733 | 45 | 44 | 2421.4 | 1.0019 | 77 | 736 | 48 | 55 | 2485.3 | 1.00295 |
| 10 | 84 | 725 | 48 | 43 | 2366.6 | 1.0015 | 81 | 730 | 50 | 54 | 2351.5 | 1.00235 |
| 11 | 83 | 734 | 46 | 46 | 2424.5 | 1.0018 | 81 | 734 | 47 | 49 | 2279.1 | 1.00305 |
| 12 | 84 | 730 | 43 | 42 | 2296.6 | 1.00275 | 86 | 727 | 42 | 51 | 2619.7 | 1.00225 |
| 13 | 86 | 726 | 54 | 54 | 2418.3 | 1.00155 | 87 | 716 | 57 | 65 | 2498 | 1.00145 |
| 14 | 86 | 726 | 46 | 42 | 2559 | 1.00235 | 77 | 740 | 44 | 61 | 2261.9 | 1.0021 |
| 15 | 86 | 718 | 54 | 47 | 2507.7 | 1.00125 | 87 | 734 | 43 | 53 | 2609.7 | 1.0031 |
| 16 | 85 | 741 | 41 | 42 | 2144.1 | 1.0018 | 85 | 734 | 46 | 53 | 2542.7 | 1.0031 |
| 17 | 85 | 733 | 50 | 53 | 2545.9 | 1.00185 | 98 | 769 | 31 | 63 | 899.4 | 1.0039 |
| 18 | 82 | 736 | 42 | 43 | 2424.5 | 1.0024 | 95 | 797 | 27 | 53 | 957.1 | 1.0039 |
| COMPETITOR | 81 | 728 | 49 | 43 | 2491.6 | 1.0017 | 696 | 723 | * | * | 561 | 1.01005 |

RESPONSE TIMES ARE INFINITE FOR THE COMPETITOR PART AT 90 HOURS OF AGING
VMin - VOLTAGE AT LEAN EXHAUST GAS CONDITIONS (MILLIVOLTS)
VMax - VOLTAGE AT RICH EXHAUST GAS CONDITIONS (MILLIVOLTS)
LRTime - TIME FOR THE SENSOR TO CHANGE FROM 300 TO 600 MILLIVOLTS AS THE EXHAUST GAS MAKES AN ABRUPT CHANGE FROM LEAN TO RICH
RLTime - TIME FOR THE SENSOR TO CHANGE FROM 600 TO 300 MILLIVOLTS AS THE EXHAUST GAS MAKES AN ABRUPT CHANGE FROM RICH TO LEAN
RESIST - THE IMPEDANCE OF THE SENSOR

FIG. 6

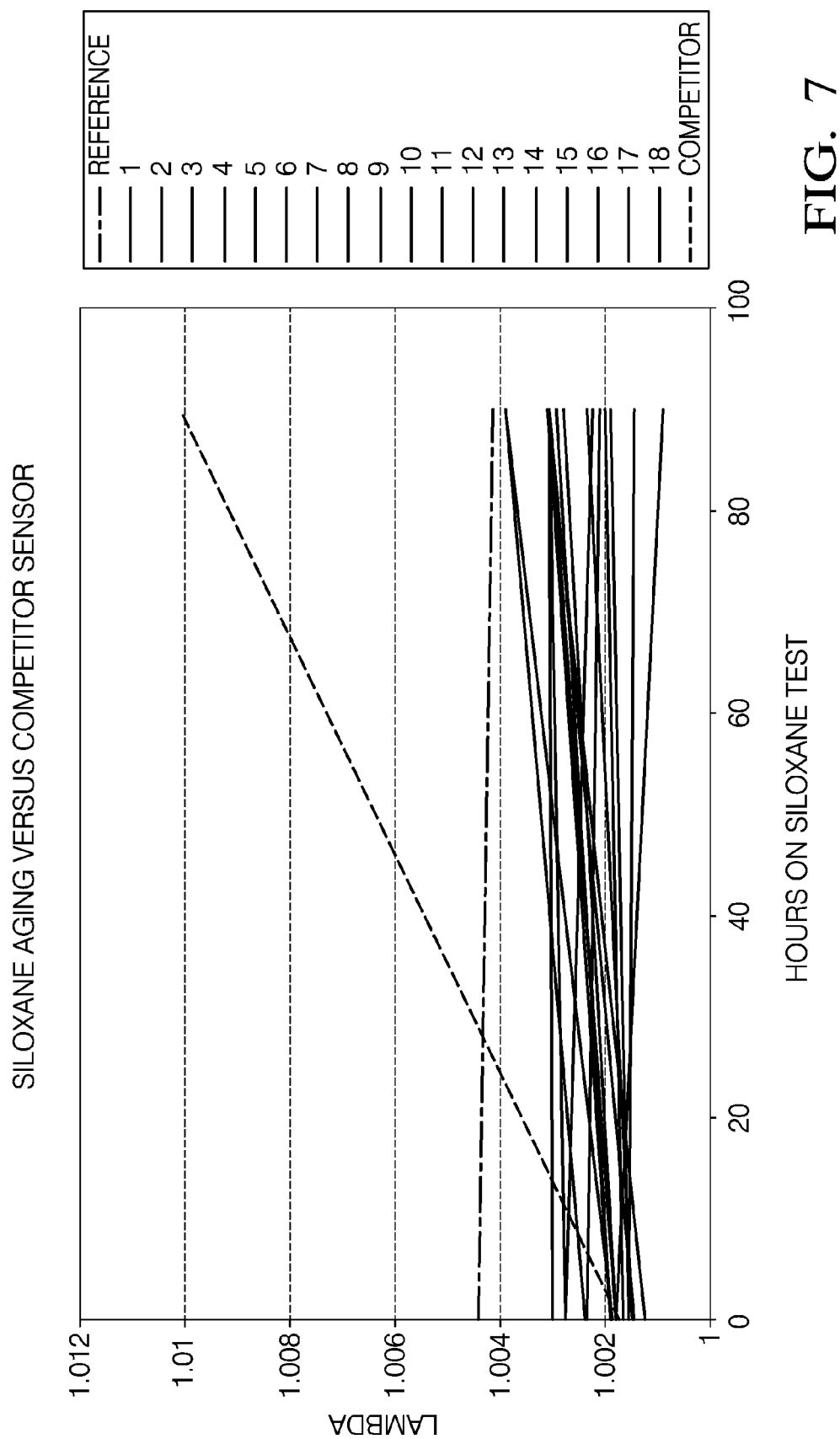

FIG. 9

SENSOR PERFORMANCE BEFORE AND AFTER HOT RICH AGING

| SENSOR NO. | 0 HOURS OF HOT RICH EXPOSURE | | | | | | 300 HOURS OF HOT RICH EXPOSURE | | | | | |
|---|---|---|---|---|---|---|---|---|---|---|---|---|
| | VMin | VMax | LRTime | RLTime | RESIST | LAMBDA | VMin | VMax | LRTime | RLTime | Resist | Lambda |
| REFERENCE | 88 | 793 | 12 | 47 | 1696.4 | 1.0041 | 90 | 787 | 13 | 49 | 1761.4 | 1.0044 |
| 1 | 79 | 719 | 50 | 45 | 2314.3 | 1.0013 | 74 | 732 | 18 | 34 | 2252.8 | 1.0013 |
| 2 | 82 | 718 | 49 | 43 | 2372.7 | 1.00075 | 80 | 739 | 15 | 36 | 2375.7 | 1.00015 |
| 3 | 82 | 719 | 53 | 46 | 2305.4 | 1.0011 | 83 | 739 | 19 | 40 | 2096.8 | 1.00025 |
| 4 | 83 | 725 | 45 | 40 | 2227 | 1.00105 | 82 | 743 | 15 | 29 | 1964.4 | 1.0006 |
| 5 | 83 | 728 | 47 | 45 | 2157.7 | 1.0012 | 82 | 734 | 24 | 31 | 1959.5 | 1.00045 |
| 6 | 82 | 726 | 43 | 39 | 2357.5 | 1.00195 | 83 | 742 | 13 | 34 | 2043.5 | 1.0006 |
| 7 | 83 | 719 | 48 | 46 | 2375.7 | 1.0017 | 83 | 737 | 18 | 31 | 2038.3 | 1.00065 |
| 8 | 82 | 730 | 42 | 43 | 2305.4 | 1.00165 | 82 | 744 | 18 | 34 | 1959.5 | 1.00045 |
| 9 | 81 | 730 | 42 | 43 | 2299.5 | 1.00125 | 79 | 737 | 19 | 33 | 2311.4 | 1.001 |
| 10 | 80 | 719 | 49 | 44 | 2241.2 | 1.0017 | 80 | 751 | 12 | 31 | 1905.8 | 1.0011 |
| 11 | 83 | 724 | 46 | 41 | 2227 | 1.0016 | 82 | 751 | 17 | 33 | 1819 | 1.0013 |
| 12 | 80 | 722 | 50 | 44 | 2360.5 | 1.00105 | 79 | 743 | 16 | 35 | 2235.5 | 1.00005 |
| 13 | 83 | 735 | 42 | 41 | 1947.1 | 1.0011 | 83 | 736 | 22 | 40 | 1891.3 | 1.0001 |
| 14 | 85 | 705 | 58 | 57 | 2462.3 | 1.00115 | 82 | 740 | 15 | 33 | 1979.5 | 1.0003 |
| 15 | 80 | 719 | 46 | 44 | 2575.5 | 1.0012 | 81 | 737 | 13 | 33 | 2320.3 | 1.0003 |
| 16 | 82 | 714 | 56 | 51 | 2168.7 | 1.00095 | 81 | 738 | 20 | 35 | 1961.9 | 1 |
| 17 | 76 | 732 | 42 | 42 | 2305.4 | 1.00125 | 77 | 740 | 18 | 38 | 2177.1 | 1.0006 |
| COMPETITOR | 72 | 753 | 13 | 41 | 121.9 | 1.00105 | 82 | 749 | 16 | 25 | 119.4 | 1.00105 |

VMin - VOLTAGE AT LEAN EXHAUST GAS CONDITIONS (MILLIVOLTS)
VMax - VOLTAGE AT RICH EXHAUST GAS CONDITIONS (MILLIVOLTS)
LRTime - TIME FOR THE SENSOR TO CHANGE FROM 300 TO 600 MILLIVOLTS AS THE EXHAUST GAS MAKES AN ABRUPT CHANGE FROM LEAN TO RICH
RLTime - TIME FOR THE SENSOR TO CHANGE FROM 600 TO 300 MILLIVOLTS AS THE EXHAUST GAS MAKES AN ABRUPT CHANGE FROM RICH TO LEAN
RESIST - THE IMPEDANCE OF THE SENSOR

SENSOR PERFORMANCE BEFORE AND AFTER RAPID AGING TEST (RAT AGING)

| SENSOR NO. | 0 HOURS RAT AGING | | | | | | | 300 HOURS RAT AGING | | | | | | |
|---|---|---|---|---|---|---|---|---|---|---|---|---|---|
|  | VMin | VMax | LRTime | RLTime | RESIST | LAMBDA | | VMin | VMax | LRTime | RLTime | RESIST | LAMBDA |
| REFERENCE | 88 | 793 | 12 | 48 | 1757.1 | 1.00445 | | 89 | 789 | 13 | 52 | 1633.8 | 1.004 |
| 1 | 77 | 730 | 44 | 43 | 2354.5 | 1.0015 | | 75 | 745 | 6 | 25 | 2048.7 | 1.0016 |
| 2 | 82 | 721 | 46 | 44 | 2369.6 | 1.0013 | | 79 | 752 | 8 | 28 | 1961.9 | 1.0015 |
| 3 | 82 | 739 | 43 | 41 | 2198.9 | 1.00195 | | 79 | 764 | 7 | 26 | 1867.7 | 1.00205 |
| 4 | 84 | 729 | 42 | 43 | 2284.9 | 1.00165 | | 82 | 753 | 7 | 26 | 1823.6 | 1.0015 |
| 5 | 81 | 729 | 42 | 42 | 2424.5 | 1.00275 | | 80 | 750 | 9 | 30 | 1898.5 | 1.0014 |
| 6 | 79 | 718 | 47 | 43 | 2510.9 | 1.00145 | | 73 | 733 | 7 | 27 | 2481.6 | 1.001 |
| 7 | 82 | 729 | 41 | 42 | 2363.6 | 1.0026 | | 79 | 740 | 7 | 25 | 2121.1 | 1.00095 |
| 8 | 85 | 739 | 42 | 45 | 2133.3 | 1.0015 | | 83 | 752 | 9 | 29 | 1758.4 | 1.001 |
| 9 | 80 | 726 | 45 | 42 | 2287.8 | 1.00135 | | 79 | 764 | 7 | 26 | 1743 | 1.0016 |
| 10 | 80 | 735 | 42 | 43 | 2354.5 | 1.0026 | | 80 | 764 | 8 | 30 | 1819 | 1.0015 |
| COMPETITOR | 71 | 778 | 15 | 49 | 59.8 | 1.0014 | | 76 | 784 | 12 | 29 | 58.4 | 1.00215 |

VMin - VOLTAGE AT LEAN EXHAUST GAS CONDITIONS (MILLIVOLTS)
VMax - VOLTAGE AT RICH EXHAUST GAS CONDITIONS (MILLIVOLTS)
LRTime - TIME FOR THE SENSOR TO CHANGE FROM 300 TO 600 MILLIVOLTS AS THE EXHAUST GAS MAKES AN ABRUPT CHANGE FROM LEAN TO RICH
RLTime - TIME FOR THE SENSOR TO CHANGE FROM 600 TO 300 MILLIVOLTS AS THE EXHAUST GAS MAKES AN ABRUPT CHANGE FROM RICH TO LEAN
RESIST - THE IMPEDANCE OF THE SENSOR

FIG. 11

CATALYST ANNEAL FOR DURABLE STOICHIOMETRIC SHIFT CORRECTED PROTECTIVE COATING FOR OXYGEN SENSORS

CROSS REFERENCE TO RELATED APPLICATIONS

This application claims the benefit of Ser. No. 60/828,946, filed Oct. 10, 2006 and entitled "CATALYST ANNEAL FOR DURABLE STOICHIOMETRIC SHIFT CORRECTED PROTECTIVE COATING FOR OXYGEN SENSORS", which is hereby incorporated by reference in its entirety.

TECHNICAL FIELD

The present invention relates to a catalyst anneal that facilitates durable stoichiometric shift correction in protective coatings for electrodes and a method of making the same. More particularly, the present invention relates to a catalyst anneal for electrodes in oxygen sensors.

BACKGROUND

Oxygen sensors located in exhaust systems of automobiles monitor the efficiency of the combustion reaction between gasoline and oxygen. When an engine operates at complete efficiency, the ratio of gasoline and oxygen is such that each reactant is completely consumed. Such reactions are deemed to be at "stoichiometry." When there is less oxygen than the stoichiometric ratio, not all of the gasoline can be consumed in the combustion reaction resulting in increased pollution and unnecessary gasoline consumption. An engine operating under such conditions is said to be running "rich." On the other hand, when there is less gasoline than required by the stoichiometric ratio, the combustion reaction will produce more nitrogen-oxide pollutants. Under these conditions, an engine is said to be running "lean." By monitoring the oxygen content of the exhaust produced in the combustion reaction, oxygen sensors send a signal to the automobile's computer indicating whether the engine is running rich or lean. The computer then adjusts gasoline intake to the engine accordingly to achieve stoichiometry. This feedback is intended to maximize fuel efficiency and minimize pollutants.

Oxygen sensors are capable of detecting the oxygen content of exhaust because they are composed of a material that is electrochemically reactive to oxygen. The signal sent to the automobile's computer is a voltage. The degree of richness or leanness relative to stoichiometry is calculated by an air to fuel ratio called lambda. In an ideal sensor, at stoichiometry, lambda will equal one. A rich mixture produces a lambda of less than one and voltages of from about 800 to 900 mV. A lean mixtures produce lambdas greater than one and voltages of from about 80 to about 150 mV.

Unfortunately, certain components of automobile exhaust such as oil detergent additives can damage oxygen sensors. To combat this problem, protective spinel coatings that guard against a variety of poisons and contaminants in the exhaust are used in oxygen sensors. The protective coatings, however, create a further problem—loss of sensor accuracy and specifically "lean shifting." This means the sensor gives a lean signal even though the mixture is stoichiometric or slightly rich. Differing diffusion rates among the various components in exhaust cause the lean shift. More specifically, the sensor responds to the presence of a small amount of hydrogen that moves faster relative to other exhaust components. Finally, carbon and hydrocarbon contamination of the protective coating can cause a variation in shifts due to the cycle of collection/burning off.

In response to the shifting problems created by the protective coatings the prior art has, in some cases, added a catalyst to the protective coating to react with free hydrogen and hydrocarbons. By facilitating an equilibrium of the various contaminant species, the catalyst prevents the differing diffusion rates that cause shifts, especially lean shifts. While this solution presents advantages over using a protective coating alone, the use of a catalyst presents further drawbacks. First, the catalyst infused protective coating causes slowing of sensor response, especially when exhaust is becoming lean from a rich condition. Second, this solution lacks durability. Catalytic poisons, such as silicon containing compounds, destroy the catalytic properties of the catalyst and thereby destroy its shift correcting capabilities.

It would therefore be desirable to provide a protective coating for sensors that either eliminates or minimizes the disadvantages of the prior art.

In particular, it would be advantageous to provide a protective coating for sensors, which will correct lean and/or rich shifting while simultaneously maintaining sensor response time. It would also be desirable to provide a protective coating for sensors, which will provide durable correction of lean and/or rich shifting without any reduction of sensor response time.

SUMMARY OF THE INVENTION

Disclosed is a protective coating for oxygen sensors, a sensor comprising the disclosed protective coating, and methods for making the same.

In one embodiment, a protective coating for an electrode of a sensor is described, the protective coating comprising an annealed catalyst, said annealed catalyst comprising at least one metal that has been subjected to thermal energy that is at least equivalent to or greater than that received from calcining the at least one metal for 24 hours at a temperature of 930 degrees C in air. In another embodiment, the annealed catalyst will comprise at least one metal that has been subjected to thermal energy that is equal to or less than that received from calcining the at least one metal for 24 hours at 1030 degrees C in air. In one exemplary embodiment, the annealed catalyst will comprise at least one metal that has been subjected to thermal energy that is equal to that received from calcining the at least one metal for 24 hours at 980 degrees C in air. In another exemplary embodiment, the annealed catalyst will comprise at least one metal catalyst that has been subjected to thermal energy that is equal to that received from calcining the at least one metal for 24 hours at 1005±25 degrees C.

In another exemplary embodiment, a sensor is described. The sensor includes: a sensing electrode having a first and second side and a first electrical lead in electrical communication with said sensing electrode; a reference electrode having a first and second side and a second electrical lead in electrical communication with said reference electrode; an electrolyte disposed between and in intimate contact with said first side of said sensing electrode and said first side of said reference electrode; and a first protective coating having a first and second side said first side disposed adjacent to said second side of said sensing electrode, said first coating comprising the disclosed annealed catalyst.

In yet another embodiment, a method for making a protective coating comprising an annealed catalyst is described. The method includes: providing a mixture comprising: (i) a metal catalyst selected from the group of rhodium, platinum, palladium, and mixtures thereof, and (ii) an alumina powder; and subjecting said mixture to thermal energy to provide an annealed catalyst, wherein the thermal energy is either equivalent to or greater than that received from calcining the mixture for 24 hours at a temperature of 930 degrees C for 24 hours in air but no greater than that received from calcining the mixture for 24 hours at 1030 degrees C in air. In another embodiment, the disclosed method further comprises mixing the annealed catalyst with a slurry comprising alumina to provide an annealed catalyst slurry.

In still another exemplary embodiment, a method for making a sensor is provided. The sensor includes: providing a sensing electrode having a first and second side and a first electrical lead in electrical communication with said sensing electrode; providing a reference electrode having a first and second side and a second electrical lead in electrical communication with said reference electrode; disposing an electrolyte between said first side of sensing electrode and said first side of reference electrode; mixing the disclosed annealed catalyst and alumina comprising slurry to provide an annealed catalyst slurry; applying said annealed catalyst slurry to said second side of said sensing electrode to provide a coated element; and calcining the coated element at a temperature of at least 700 degrees C. for a time of at least 2 hours to form a first protective coating having a first and second side said first side disposed adjacent to said sensing electrode second side. In another embodiment, the disclosed method of making a sensor further comprises coating the first protective coating with an alumina only protective slurry coating to provide a coated first protective coating that is then calcined again at a temperature of at least 700 degrees C. for a time of at least 2 hours to form a sensor element having a second protective coating.

BRIEF DESCRIPTION OF THE DRAWINGS

Referring now to the figures, which are meant to be exemplary, not limiting, and wherein like elements are numbered alike in several figures.

FIGS. 5a and 5b are tables illustrating the performance characteristics of sensors comprising various embodiments of the disclosed annealed catalysts.

FIG. 6 is a table comparing sensors comprising the disclosed annealed catalysts again a reference sensor and a competitive sensor in a Siloxane Aging Test.

FIG. 7 is a graphical illustration comparing sensors comprising the disclosed annealed catalysts again a reference sensor and a competitive sensor in a Siloxane Aging Test.

FIG. 9 is a table comparing sensors comprising the disclosed annealed catalysts again a reference sensor and a competitive sensor in a Hot Rich Aging Test.

FIG. 11 is a table comparing sensors comprising the disclosed annealed catalysts again a reference sensor and a competitive sensor in a RAT Aging Test.

DETAILED DESCRIPTION OF EXEMPLARY EMBODIMENTS

A protective coating for gas sensors, in particular oxygen sensors, comprising a first protective coating layer, is formed from an annealed catalyst and a slurry comprising an alumina. Although described in connection with an oxygen sensor, it is to be understood that the protective first coating can be employed with any type of sensor such as a nitrogen oxide sensor, hydrogen sensor, hydrocarbon sensor, or the like. Furthermore, while oxygen is the reference gas used in the description disclosed herein, it should be understood that other gases could be employed as a reference gas.

Figure 1:
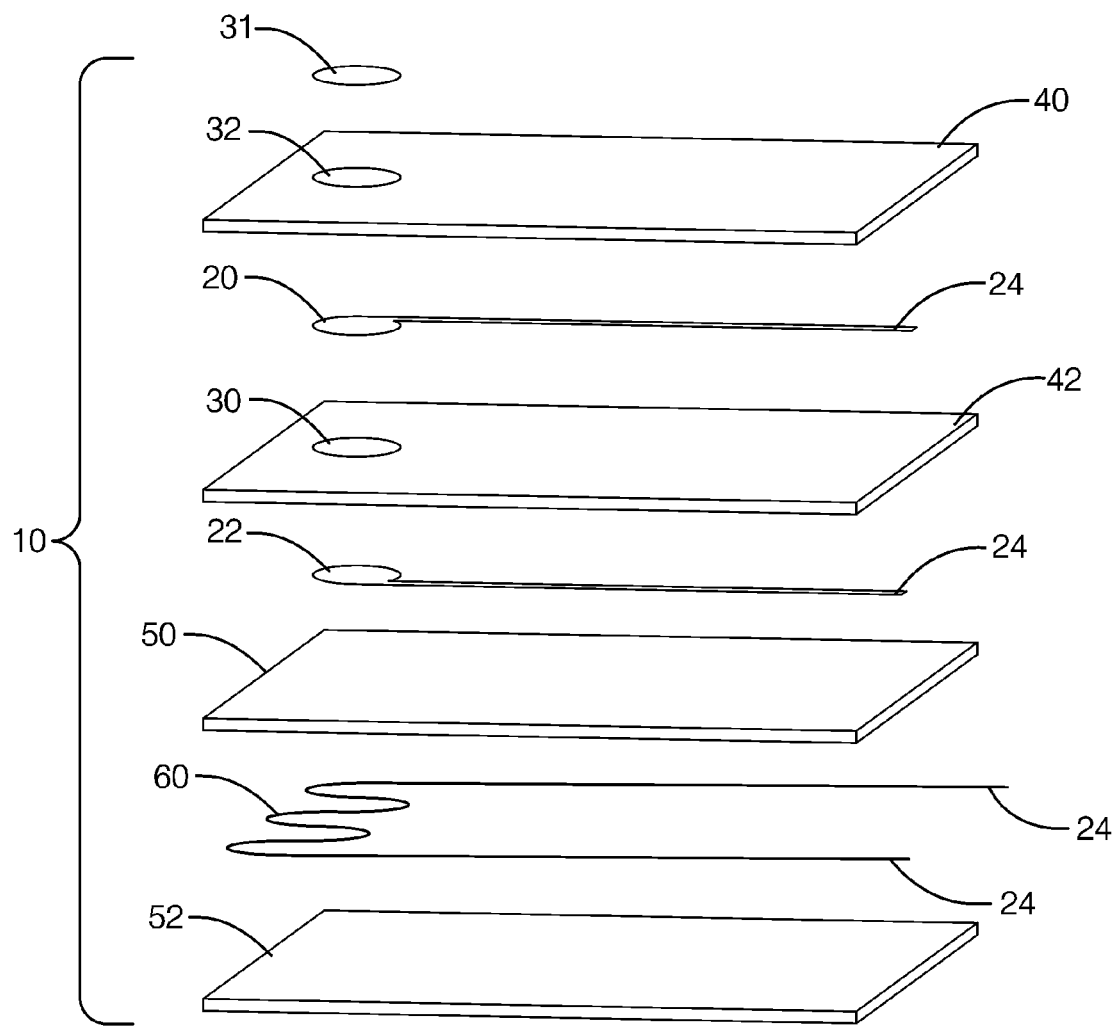
FIG. 1 is an expanded isometric view of one embodiment of an oxygen sensor.

Referring to FIG. 1, the sensor element 10 is illustrated. The exhaust gas (or outer) electrode 20 and the reference gas (or inner) electrode 22 are disposed on opposite sides of, and adjacent to, an electrolyte layer 30 creating an electrochemical cell (20/30/22). On the side of the exhaust gas electrode 20 opposite solid electrolyte 30 is an optional protective insulating layer 40 with a porous section 32 that enables fluid communication between the exhaust gas electrode 20 and the exhaust gas. The disclosed protective coating 31 is disposed over the porous section 32. The electrolyte 30 and the porous section 32 can be disposed adjacent to, or as inserts within, layers 40, 42, respectively. Meanwhile, disposed on a side of the reference electrode 22 opposite electrolyte layer 30 is a heater 60. Typically disposed between the reference gas electrode 22 and the heater 60, as well as on a side of the heater 60 opposite the reference gas electrode 22, are one or more insulating layers 50, 52.

In addition to the above sensor components, conventional components can be employed, including but not limited to lead gettering layer(s), leads, contact pads, ground plane(s), support layer(s), additional electrochemical cell(s), and the like. The leads (24), which supply current to the heater and conduct signals from the electrodes (20) and (22), are typically formed on the same layer as the heater/electrode to which they are in electrical communication and extend from the heater/electrode to the terminal end of the gas sensor where they are in electrical communication with the corresponding via system and appropriate contact pads as are known in the art.

Insulating layers 50, 52, and protective layer 40, provide structural integrity (e.g., protect various portions of the gas sensor from abrasion and/or vibration, and the like, and provide physical strength to the sensor), and physically separate and electrically isolate various components. The insulating layer(s), which can be formed using ceramic tape casting methods or other methods such as plasma spray deposition techniques, screen printing, stenciling and others conventionally used in the art, can each be up to about 200 microns thick or so, with a thickness of about 50 microns to about 200 microns. Since the materials employed in the manufacture of gas sensors preferably comprise substantially similar coefficients of thermal expansion, shrinkage characteristics, and chemical compatibility in order to minimize, if not eliminate, delamination and other processing problems, the particular material, alloy or mixture chosen for the insulating and protective layers is dependent upon the specific electrolyte employed. Typically these insulating layers comprise a dielectric material such as alumina, and the like.

Disposed between the insulating layers 50, 52, is a heater 60 that is employed to maintain the sensor element at the desired operating temperature. Heater 60 can be any conventional heater capable of maintaining the sensor end at a sufficient temperature to facilitate the various electrochemical reactions therein. The heater 60, which is typically platinum, palladium, and the like, as well as oxides, mixtures, and alloys comprising at least one of the foregoing metals, or any other conventional heater, is generally screen printed or otherwise disposed onto a substrate to a thickness of about 5 microns to about 50 microns.

Disposed on the side of insulating layer 50 opposite to heater 60 is the electrolyte 30. The electrolyte 30 can be solid or porous, can comprise the entire layer or a portion thereof, can be any material that is capable of permitting the electrochemical transfer of oxygen ions, should have an ionic/total conductivity ratio of approximately unity, and should be compatible with the environment in which the gas sensor will be utilized (e.g., up to about 1,000° C.). Possible electrolyte materials can comprise any material conventionally employed as sensor electrolytes, including, but not limited to, zirconia which may optionally be stabilized with calcium, barium, yttrium, magnesium, aluminum, lanthanum, cesium, gadolinium, and the like, as well as combinations comprising at least one of the foregoing materials. For example, the electrolyte can be alumina and/or yttrium stabilized zirconia. Typically, the electrolyte, which can be formed via many conventional processes (e.g., die pressing, roll compaction, stenciling and screen printing, tape casting techniques, and the like), has a thickness of up to about 500 microns or so, with a thickness of about 25 microns to about 500 microns preferred, and a thickness of about 50 microns to about 200 microns especially preferred.

It should be noted that the electrolyte layer 30 and porous section 42 can comprise an entire layer or a portion thereof; e.g., they can form the layer (i.e., 42 and 40, respectively), be attached to the layer (porous section/electrolyte abutting dielectric material), or disposed in an opening in the layer (porous section/electrolyte can be an insert in an opening in a dielectric material layer). The latter arrangement eliminates the use of excess electrolyte and protective material, and reduces the size of gas sensor by eliminating layers. Any shape can be used for the electrolyte and porous section, with the size and geometry of the various inserts, and therefore the corresponding openings, being dependent upon the desired size and geometry of the adjacent electrodes. It is preferred that the openings, inserts, and electrodes have a substantially compatible geometry such that sufficient exhaust gas access to the electrode(s) is enabled and sufficient ionic transfer through the electrolyte is established.

The electrodes 20, 22, are disposed in ionic contact with the electrolyte layer 30. Conventional electrodes can comprise any catalyst capable of ionizing oxygen, including, but not limited to, materials such as platinum, palladium, osmium, rhodium, iridium, gold, ruthenium, zirconium, yttrium, cerium, calcium, aluminum, silicon, and the like, and oxides, mixtures, and alloys comprising at least one of the foregoing catalysts. As with the electrolyte, the electrodes 20, 22 can be formed using conventional techniques. Some possible techniques include sputtering, painting, chemical vapor deposition, screen printing, and stenciling, among others. If a co-firing process is employed for the formation of the sensor, screen printing the electrodes onto appropriate tapes is preferred due to simplicity, economy, and compatibility with the co-fired process. Electrode leads (not shown) and vias (not shown) in the insulating and/or electrolyte layers are typically formed simultaneously with electrodes.

Figure 2:
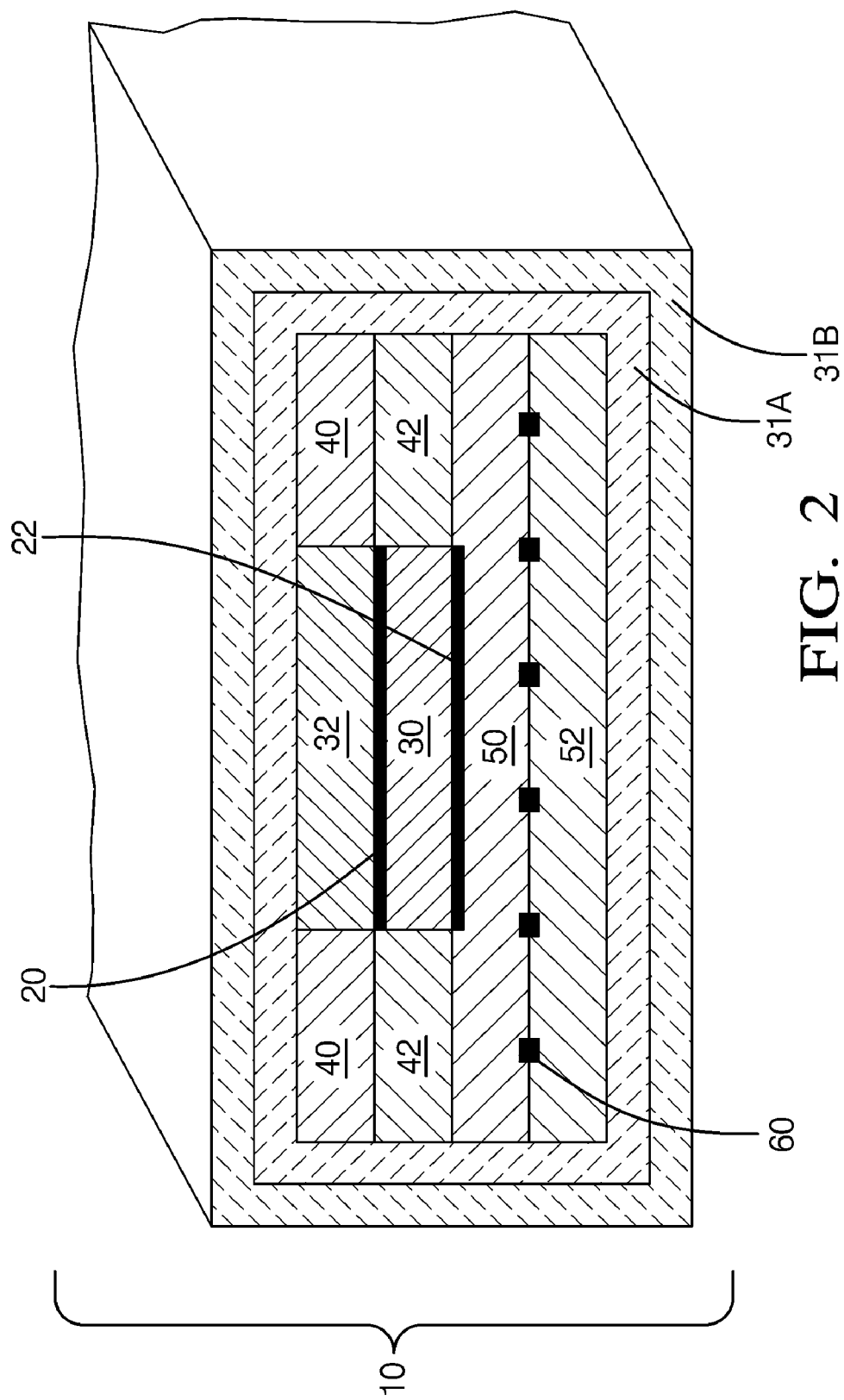
FIG. 2 is a cross sectional isometric view of one embodiment of an oxygen sensor coated with the catalyst anneal and alumina protective coatings of the invention.

Following the formation of the sensing element 10, a protective coating 31 as disclosed herein is applied to the sensing element 10. This protective coating comprises a first coating 31a and a second optional coating 31b, as shown in FIG. 2. It will be appreciated that the protective coating 31 may or may not surround the entire sensor 10 as shown in FIG. 2. The first protective coating 31a may be in direct physical contact with electrode 20 or optional porous section 32 and additionally may optionally coat a portion of or all of substrate layer 40 and/or support layer 52.

The first protective coating 31a comprises an annealed catalyst. As contained herein "annealed catalyst" describes a catalytic material treated with a particular amount of thermal energy. In one embodiment, the annealed catalyst is allowed to cool very slowly and uniformly. The annealing process changes the properties of the catalyst and specifically reduces the catalytic activity of the catalyst. Without being held to theory, it is believed that the reduced catalytic activity of the annealed catalyst allows for faster sensor response times while still providing stoichiometric shift correction.

In general, it has been found that a suitable amount of thermal energy is obtained from subjecting the disclosed metal catalysts to temperatures of from 930 to 1030 degrees C. for periods of from 10 to 48 hours. To obtain an annealed catalyst exhibiting the proper level of catalytic activity, a catalyst will, in general, be calcined so that it is subject to an amount of thermal energy that is either equivalent to or greater than that received from exposure to a temperature of 930 degrees C. for a time of from 24 to 48 hours in air but which is no greater than that received from exposure to a temperature of 1030 degrees C. for a period of from 10 to 48 hours in air.

It will be appreciated that as the temperature of exposure is elevated, the required time of exposure will decrease. For example, if the metal catalyst is heated at a temperature of 930 degrees C., then a minimum of 24 hours exposure to that temperature is required for the metal catalyst to be subjected to adequate thermal energy. Alternatively, if the metal catalyst is heated at a temperature of 1030 degrees C., then the minimum number of hours of exposure to that temperature necessary for the metal catalyst to be subjected to adequate thermal energy is only 10 hours. If the metal catalyst is heated at a temperature of 980 degrees C., then a minimum of 24 hours exposure to that temperature is required for the metal catalyst to be subjected to adequate thermal energy. However, it is believed that a maximum of 48 hours is suitable for all of the foregoing temperatures.

In one exemplary embodiment, the disclosed metal catalyst compositions will be heated or calcined for a time of from 10 to 48 hours at a temperature of from 980 to 1030 degrees C. In another exemplary embodiment, the disclosed metal catalyst compositions will be heated or calcined for a time of from 24 to 48 hours at a temperature of about 1005±25 degrees C. In one exemplary embodiment, the annealed catalyst will comprise at least one catalyst that has been subjected to thermal energy that is equal to that received from calcining for 24 hours at 980 degrees C. in air. In another exemplary embodiment, the annealed catalyst will comprise at least one catalyst that has been subjected to thermal energy that is equal to that received from calcining the at least one metal 1005±25 degrees C. for a time of about 24 hours.

Figure 4:
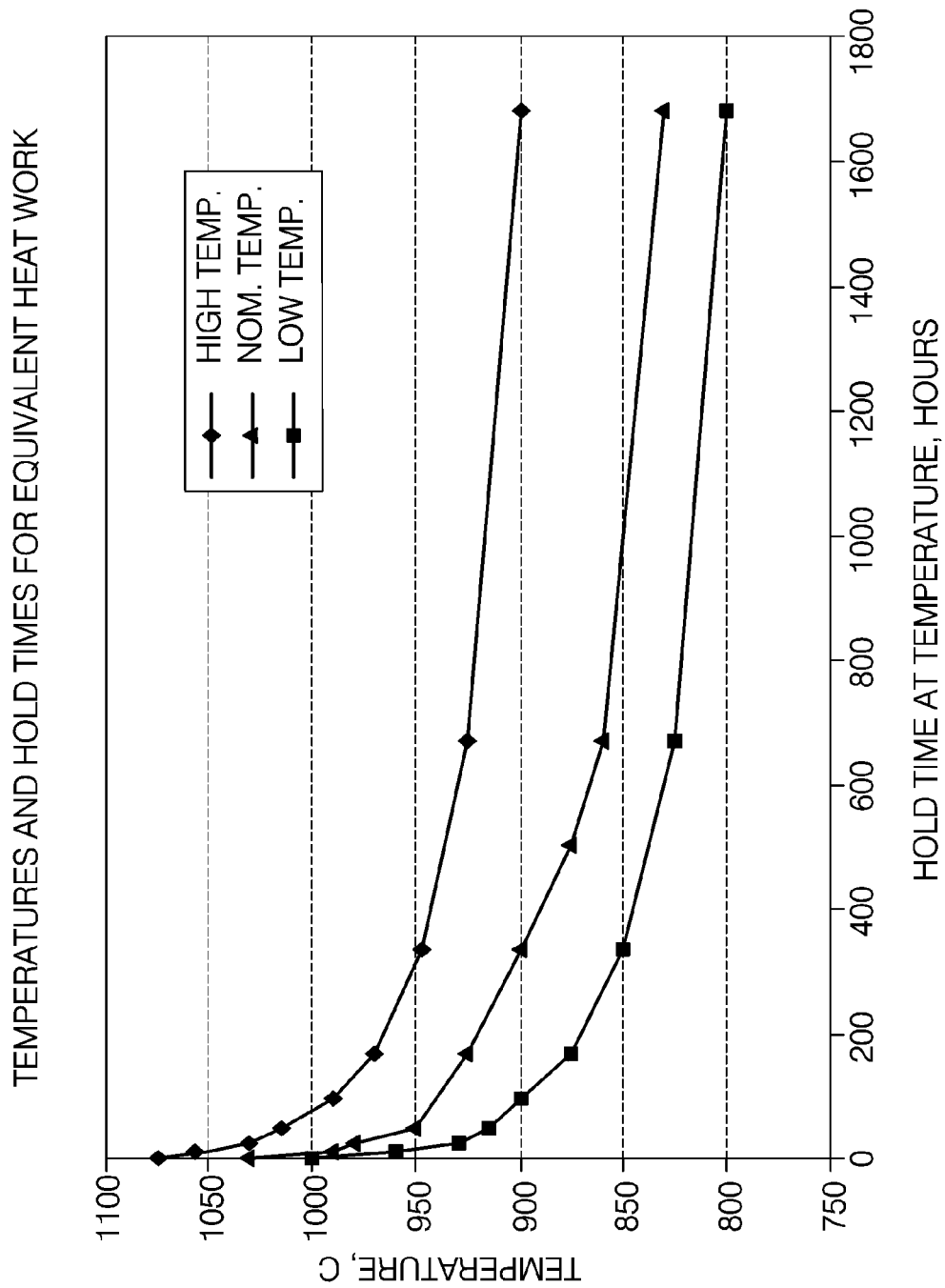
FIG. 4 is a graph showing temperatures and hold times for equivalent heat work.

It will be appreciated that these time and temperature profiles define only the appropriate amounts of thermal energy. That is, as shown in FIG. 4, other temperatures and hold time profiles are suitable and may be used to obtain the required amount of thermal energy.

For example, the minimum thermal energy may also be obtained by calcining a suitable catalyst for 1700 hours at a temperature of 800 degrees C. Alternatively, the maximum thermal energy may also be obtained by calcining a suitable catalyst for 1700 hours at 900 degrees C. Finally, a particularly suitable amount of thermal energy may be obtained by calcining a suitable catalyst for 1700 hours at 825 degrees C. FIG. 4 was obtained using the Cone Calculation Program available from Orton.

Examples of catalytic materials suitable for use in making the disclosed annealed catalyst include one or more metals selected from platinum, rhodium, palladium, and mixtures thereof. In an exemplary embodiment, the catalyst will be platinum.

In one exemplary embodiment, suitable catalyst materials will be one or more suitable metals that are finely divided. In one embodiment, finely divided metals are those obtained from depositing a 5 wt % salt solution on a suitable alumina powder (ii) as described below.

In one embodiment, a method for making an annealed catalyst comprises mixing a suitable metal catalyst (i) with an alumina powder (ii). The amount of catalyst (i) is not critical and is based on the amount of catalyst desired on the final protective coating as discussed below, i.e., after calcining an annealed catalyst slurry to obtain the first protective coating. In one embodiment, the metal catalyst will be present in the mixture in an amount of about 5 wt % Pt, based on the total amount of the mixture.

Suitable alumina powder (ii) for use in the mixture are those alumina powders comprising transition phase alumina powders. Transition phase aluminas are those, which are reproducible and stable at room temperature. Transition phase aluminas include gamma, delta, theta, kappa, eta, rho, and chi aluminas. These transition phase aluminas may optionally be stabilized with an alkaline earth metal and/or a lanthanide metal, or a compound, oxide, or combination comprising at least one of the foregoing stabilizers.

In embodiment, the alumina powder (ii) comprises from 1 to 100% by weight transition phase alumina powder, based on the total weight of the alumina powder (ii). In another embodiment, the alumina powder (ii) will comprise from at least 60 to 100% transition phase alumina powder. In one exemplary embodiment, the alumina powder (ii) comprises 100% transition phase alumina powder, based on the total weight of the alumina powder (ii).

In one embodiment, the alumina powder (ii) will comprise a transition phase alumina powder that is stabilized from 0 to 100%, based on the total amount of the transition phase alumina powder. In one embodiment, the alumina powder (ii) will comprise a transition phase alumina powder that is stabilized from at least 60 to 100%, based on the total amount of the transition phase alumina powder. In one embodiment, the alumina powder (ii) will comprise a transition phase alumina powder that is 100% stabilized, based on the total amount of the transition phase alumina powder.

In one exemplary embodiment, the transition phase alumina comprises lanthanum stabilized transition phase alumina.

In one especially exemplary embodiment, the alumina powder (ii) will comprise high surface areas transition phase alumina powders. As used herein "high surface area alumina" refers to alumina having a surface area of at least 50 m2/g or more. In one embodiment, the high surface alumina will have a surface of 80 m2/g or more. In one exemplary embodiment, high surface area alumina will have a surface area of 100 m2/g or more. Without being held to theory, it is believed the high porosity—and hence high surface area—combined with the adsorption properties of the transition phase aluminas serve to remove the catalytic poisons present in exhaust gas thereby prolonging the durability of the first coating and the sensor overall. This latter statement is believed to be true regardless whether it is alumina powder (ii), or alumina slurry (iii) or (iv).

With respect to making the disclosed embodiment, disposition of the catalyst as described above on an alumina powder can take place by various means conventional in the art including vapor phase deposition, use of a water-soluble salt of the catalyst, sputtering, or milling. In one exemplary embodiment, the disposition method comprises the use of a water-soluble salt of the catalyst.

In one embodiment, the metal catalyst (i) comprises from 0.1 to 50 wt % of the alumina powder, based on the total weight of the alumina powder (ii) and metal catalyst (i). In another embodiment, the catalyst comprises from 1 to 10 wt % of the alumina powder, based on the total weight of the alumina powder and the metal catalyst (i). In one exemplary embodiment, the catalyst comprises from 2 to 7 wt % of the alumina powder, based on the total weight of the alumina powder (ii) and the metal catalyst (i). In one exemplary embodiment, the catalyst comprises about 5 wt % of the alumina powder, based on the total weight of the alumina powder (ii) and the metal catalyst (i).

The resulting mixture is then subjected to thermal energy to provide an annealed catalyst. As disclosed above the amount of thermal energy is either equivalent to or greater than that received from calcining the mixture for a minimum of 24 hours at a temperature of 930 degrees C for 24 hours in air but is no greater than that received from calcining the mixture for 48 hours at 1030 degrees C. in air. In one exemplary embodiment, the annealed catalyst will comprise a mixture of catalyst (i) and alumina powder (ii) that has been subjected to thermal energy that is equal to that received from calcining the resulting mixture for 24 hours at 1005±25 degrees C.

Calcining of the metal catalyst (i) or the mixture of metal catalyst (i) and the alumina powder (ii) will generally occur in filtered air environment in a commercially available oven or kiln. Suitable examples include a box kiln such as a Lindberg Model CC58114C.

In one embodiment, the method of making the annealed catalyst protective coating will further comprise reducing the particle size of the annealed catalyst. For example, in one embodiment, the annealed catalyst will be reduced to a particle size of less 250 microns, especially less 100 microns and in one exemplary embodiment less than 75 microns. Reduction of the calcined catalyzed alumina powder to the desired particle size may take place by any means conventional in the art including milling and classification by sieving.

The resulting annealed catalyst is then mixed with an alumina slurry (iii) comprising alumina to provide an annealed catalyst slurry.

Suitable alumina slurries (iii) are those comprising alumina and water. Alumina refers to a substance containing the Al2O3 stoichiometric formula. Alpha alumina is the only thermodynamically stable oxide of aluminum and refers to hexagonal close packed and related structures. Slurry (iii) may also comprise low surface areas alumina. As used herein "low surface area alumina" refers in one embodiment to those alumina having a surface area equal to or less than 30 m2/g. In one exemplary embodiment, low surface area alumina refers to alumina having a surface area of about 10 m2/g of surface area. In one embodiment, suitable alumina slurries (iii) comprise a mixture of alpha alumina and a transition phase alumina as defined above for slurry (ii).

In one embodiment, the slurry (iii) will comprise sufficient transition phase alumina such that after: (a) mixing slurry (iii) with the annealed catalyst to provide the annealed catalyst slurry, and (b) calcining the annealed catalyst slurry to provide first protective coating 31a; the resulting first protective coating 31a will comprise from 20 wt % to 90 wt % transition phase alumina based on the total weight of alumina contained in the first protective coating 31a.

In one embodiment, when mixing the annealed catalyst and alumina slurry (iii), water may be present in amount of from 30 to 60 wt %, based on the total weight of the slurry (iii). In one exemplary embodiment, when mixing the annealed catalyst and alumina slurry (iii), the water will generally comprise 50 wt % based on the total weight of the slurry (iii). The percentage of water, however, does not need to be precise.

In one embodiment, the metal catalyst as % metal may be present in the annealed catalyst slurry (i.e., annealed catalyst+alumina slurry (iii)) at a concentration of from 20-90% multiplied by the concentration of the metal in the mixture (i.e., mixture of metal catalyst (i) and alumina powder (ii)) before subjecting it to the appropriate amount of thermal energy.

In one embodiment, the annealed catalyst slurry comprises from 0.10 wt % to 10.00 wt % metal based on the total weight of the annealed catalyst slurry. In one embodiment, the annealed catalyst slurry comprises from 0.20 wt % to 1.50 wt % metal based on the total weight of the annealed catalyst slurry. In one embodiment, the annealed catalyst slurry comprises from 0.25 wt % to 0.75 wt % metal based on the total weight of the annealed catalyst slurry. In one embodiment, the annealed catalyst slurry comprises from 0.25 wt % to 0.45 wt % metal based on the total weight of the annealed catalyst slurry.

The resulting annealed catalyst slurry may be disposed or applied to a sensor element and subsequently calcined or fired to provide a first protective coating 31a.

In one embodiment, the annealed catalyst slurry will comprise sufficient annealed catalyst so as to provide a weight of from 0.05 to 3 wt % metal catalyst in the final first protective coating 31a, based on the total weight of the first protective coating 31a, i.e, after firing of the annealed catalyst slurry to make the first protective coating 31a. In another embodiment, the annealed catalyst slurry will comprise sufficient annealed catalyst so as to provide a weight of from 0.10 to 1.00 wt % metal in the final first protective coating 31a, based on the total weight of the first protective coating 31a. In one exemplary embodiment, the annealed catalyst slurry will comprise sufficient annealed catalyst so as to provide a weight of from 0.20 to 1.00 wt % metal in the final first protective coating 31a, based on the total weight of the first protective coating 31a. In another exemplary embodiment, the annealed catalyst slurry will comprise sufficient annealed catalyst so as to provide a weight of from 0.50 to 0.075 wt % metal in the final first protective coating 31a, based on the total weight of the first protective coating 31a.

The first protective coating 31a should have a thickness of 0.01 mm to 0.25 mm. In one exemplary embodiment, the coating 31a will have a thickness of from 0.10 to 0.25 mm. In another embodiment, the coating 31a may have a thickness of from 0.05 to 0.15 mm.

The second optional protective coating 31b of the invention is disposed on a second side of the first protective coating 31a opposite electrode 20 or the optional porous section 32. In one exemplary embodiment, second protective coating 31b is not optional and is present as described in FIG. 2.

In one embodiment, the second coating before calcining comprises a slurry mixture (iv) of high surface area transition phase alumina as defined above for slurry (ii) and a lower surface area alpha alumina as defined above with regards to slurry (iii), and water.

In one exemplary embodiment, the slurry (iv) will comprise a high concentration of high surface areas transition phase alumina as defined above. In one embodiment, the second protective coating 31b will result from the calcining of a slurry (iv) comprising more than 40 weight % high surface area transition phase alumina based on the total weight of slurry (iv). In one embodiment, the second protective coating 31b will result from the calcining of a slurry (iv) comprising more than 50 weight % high surface area transition phase alumina based on the total weight of slurry (iv). In one embodiment, the second protective coating 31b will result from the calcining of a slurry (iv) comprising more than 65 weight % high surface area transition phase alumina based on the total weight of slurry (iv).

Figure 3:
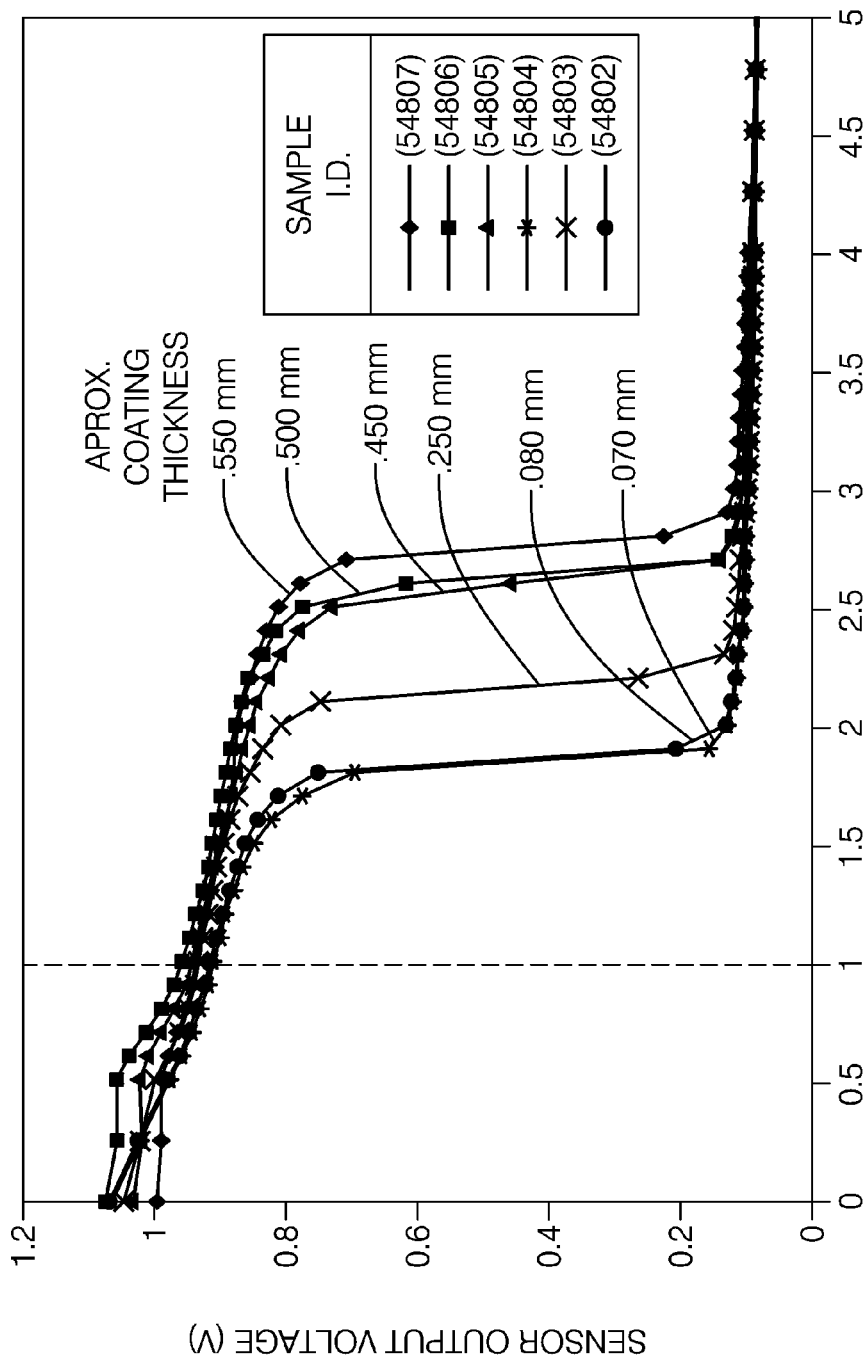
FIG. 3 is a graph illustrating the impact of dip coating thickness on the disclosed first protective coating.

In one embodiment, the second coating 31b may be present at a thickness of from 0.05 mm to 0.25 mm. In one exemplary embodiment, the second coating 31b may be present at a thickness of from 0.05 mm to 0.10 mm. Increasing the thickness of the second layer above this range will cause significant lean shifting in the sensor as illustrated in FIG. 3.

Also disclosed are additional methods of making the annealed catalyst protective coating and a sensor employing the disclosed protective coatings.

The method for making the sensor comprises: using a sensing electrode having a first and second side and a first electrical lead in electrical communication with said sensing electrode; using a reference electrode having a first and second side and a second electrical lead in electrical communication with said reference electrode; disposing an electrolyte between said first side of said sensing electrode and said first side of said reference electrode; disposing a first side of a first protective coating comprising an annealed catalyst which has been calcined adjacent to said second side of said sensing electrode; and disposing a second protective coating comprising a high surface area transition phase alumina in physical contact with a second side of said first coating.

The production of the first protective coating takes place via the deposition of the annealed catalyst slurry to the second side of the sensing electrode or any equivalent sensor element. Application of the annealed catalyst slurry may take place in any conventional fashion including imbibing, spraying, spray coating, painting, dipping, spin coating, vapor deposition, and the like. In one exemplary embodiment, application is done via dipping.

After application of the annealed catalyst slurry, the first protective coating 31a may be formed by calcining the coated sensor side or element. Calcining as used herein refers to subjecting the coated annealed catalyst slurry to a temperature of from 500 to 800 degrees C. for 1 to 4 hours or to thermal energy equivalent to this time/temperature profile. In one exemplary embodiment, the first protective coating will be formed by heating the coated annealed catalyst slurry at temperature of about 700 degrees C. for 1 to 2 hours. As discussed above, the final thickness of the first protective coating 31a will in one exemplary embodiment be between 0.10 mm and 0.25 mm.

Disposition of the second protective coating 31b on the second side of the first protective coating 31a similarly takes place via a slurry (iv) as described above. Application of the slurry (iv) may take place in any conventional fashion including imbibing, spraying, spray coating, painting, dipping, spin coating, vapor deposition, and the like. In one exemplary embodiment, application comprises dipping.

After application of the slurry (iv), the second protective coating 31b is formed by calcining the first protective coating that has been coated with the slurry (iv). Calcining as used herein refers to subjecting the coated annealed catalyst slurry to a temperature of from 500 to 800 degrees C. for 1 to 4 hours or to thermal energy equivalent to this time/temperature profile. In one exemplary embodiment, the first protective coating will be formed by heating the coated annealed catalyst slurry at temperature of about 700 degrees C. for 1 to 2 hours.

In one embodiment, the final thickness of the second protective coating 31b should be between 0.05 mm and 0.550 mm. In another embodiment, the final thickness of the second protective coating 31b should be between 0.05-mm and 0.20 mm. In one exemplary embodiment, the final thickness of the second protective coating 31b should be between 0.05 mm and 0.10 mm.

The following examples are illustrative of the claimed invention but are not intended to limit the scope of the invention.

EXAMPLES

Example 1

Sensors made with the method of the invention were tested to determine sensor response times. In these particular examples, the catalytic material comprises platinum. The impact of increased calcining times and temperatures on sensor response times were measured at various concentrations of catalytic material. Table 1 indicates these sensor response times for lean to rich transitions (LR+Lag Time) and rich to lean transitions (RL+Lag Time) RL and LR refers to the time it takes a sensor to change from lean to a rich reading. This time actually means the time the output of the sensor changes from 300 mV to 600 mV. Lag time is the time delay between the switching of the controlling sensor and the sensor being tested. Both of these times represent a response time. The concentrations of catalytic material are measured in wt % of catalyst based on the total weight of the first protective annealed catalyst coating.

TABLE 1

| | Calcining Parameters | | | |
|---|---|---|---|---|
| | 800 C. 2 hrs | | 980 C. 24 hrs | |
| Catalytic Material Concentration | LR + Lag Time (milli- seconds) | RL + Lag Time (milli- seconds) | LR + Lag Time (milli- seconds) | RL + Lag Time (milli- seconds) |
| 0.1 | 101 | 124 | 89 | 113 |
| 0.3 | 130 | 166 | 103 | 128 |
| 0.4 | 133 | 197 | 106 | 135 |

Reducing catalytic activity by higher temperature and longer calcining time improves response times especially at high concentrations of catalyst. Higher concentrations of catalysts serve to increase durability of stoichiometric shift correction.

Calcining at temperatures below 800 C. significantly increases sensor response times. Table 2 provides comparative examples wherein the platinum catalyst was calcined at 600 C. for 2 hours. Again, catalytic material concentrations are measured in wt % of catalyst based on the total weight of the first protective annealed catalyst coating.

TABLE 2

| | 600 C. 2 hrs. | |
|---|---|---|
| Catalytic Material Concentration | LR + Lag Time (milliseconds) | RL + Lag Time (milliseconds) |
| 0.0 | 8 | 26 |
| 0.0 | 17 | 31 |
| 0.02 | 64 | 40 |
| 0.02 | 52 | 25 |
| 0.02 | 81 | 57 |
| 0.05 | 76 | 55 |
| 0.05 | 104 | 90 |
| 0.05 | 98 | 75 |
| 0.30 | 205 | 253 |
| 0.30 | 196 | 247 |

The thickness of the second protective alumina coating affects the magnitude of lean shifting in the sensor. FIG. 3 indicates the impact of the second coating's thickness on the sensor output voltage. Increased thickness of the second protective alumina coating above 0.25 mm causes significant and undesirable lean shifting.

Example 2

This example evaluates the effect of metal catalyst concentration, annealing temperature and time, and the thickness of coatings 31a and 31b upon final sensor performance as measured by siloxane poisoning test.

Columns 1, 2, 3, 4, and 5 of FIGS. 5a and 5b respectively set forth the sensor #, % by weight Pt based on the first protective coating, film thickness of the first protective coating, and the film thickness of the second protective coating.

The first protective coatings set forth in Tables 5a and 5b were prepared as follows:

A base slurry (iii) of 11107 was prepared by adding 6.3 grams of deionized water to a container. 1.3 grams of Al(NO3)3*9H2O were then added to the container with water. 4.6 grams of transition phase alumina were then added to the container followed by the addition of 4.6 grams of submicron alpha alumina. The resulting mixture was then milled in a vibratory mill for 90 minutes. The density of the slurry was measured and adjusted to 1.690 g/cc. The pH of slurry (iii) was between 3.3+/−0.2. Transition phase alumina which has 5 wt % Pt and which had been annealed at the various temperatures was then added to the base slurry (iii) in the following amounts:

To make the 0 wt % Pt slurry 0 grams of 5 wt % Pt alumina was added to 16 grams of base slurry. To make the 0.02 wt % Pt slurry, 16 grams of base slurry was added to container along with 0.065 g of 5 wt % Pt alumina. For the 0.05 wt % Pt slurry, 16 grams of base slurry was added to the container along with 0.162 g of 5 wt % Pt alumina. For the 0.3 wt % Pt slurry, 16 grams of base slurry was added to the container along with 1.02 g of 5 wt % Pt alumina.

The mixtures were then mixed for 15 minutes using a magnetic stirring rod. Water was added as needed to adjust viscosity to give the desired coating thickness set forth in columns 3 and 4 of FIG. 5a. The sensing portion of the element was dipped in the slurry under controlled conditions to attain the thickness. The elements coated elements were fired at 700 degrees C. for 90 minutes.

FIGS. 5 and 5b also set forth the results for a Siloxane Poisoning Test (Delphi Test Specification ES-7929/4.5.1) that measures the resistance of an oxygen sensor to silicon poisoning. The test was conducted as follows: Fully functioning sensors were used. A silicon additive was added to a fuel (Howell EEE) so as to obtain a concentration of 1.56 ml siloxane/gallon fuel. Sensor performance was first evaluated at 0, 30, and 60 hours exposure to siloxane contaminated exhaust gas.

The second protective coating was comprised of alpha alumina, transition phase alumina and aluminum nitrate and was prepared according to the disclosures herein and was applied by dipping to the foregoing sensors.

The same sensors were then subjected to a contaminated exhaust stream as follows: An exhaust stream was produced using a 3.4 liter engine having an exhaust gas temperature of 400±15 degrees C. The engine was run using the siloxane doped fuel in a closed loop to ensure that no less than 150 gallons of the doped fuel was consumed. The sensors were exposed to the resulting exhaust stream for 30 and 60 hours and maintained at a temperature of 800 to 825 degrees C.

The data set forth in FIG. 5b illustrates that the most advantageous sensors are those comprising first protective coatings comprising from 0.30 to 0.35% by weight of platinum, wherein the annealed catalyst was made by calcining the mixture of the metal catalyst (i.e., metal (i) and the alumina slurry (ii)) at a temperature of 1005±25 degrees C. for 24 hours. The data also illustrates that advantageous sensors are those employing a first protective coating 31 having a film thickness of from 10 to 0.25 mm and a second protective coating 31b having a film thickness of from 0.50 to 0.10 mm.

Example 3

Sensors comprising an annealed catalyst (0.60 wt % Pt in the dry first protective coating 31a and annealed for 24 hours at 980 degrees C.) were evaluated against a reference oxygen sensor (a Delphi planar oxygen sensor lacking the annealed catalyst) and a competitor's planar oxygen sensor were evaluated using the Siloxane Aging Test, the Hot Rich Test and the (RAT) test.

The Siloxane Aging Test exposes oxygen sensors to an exhaust environment in which silicon compounds from engine-compartment components cause contamination. The engine was a 4.3 liter throttle body injection type or equivalent; oil was SAE 30W, API SG or equivalent; maximum oil consumption allowed was 4 quarts per 100 hours; fuel was Howell "EEE"; Siloxane SWS-03314 or equivalent was uniformly mixed with the fuel at a concentration of 1.56 ml/gallon.

The engine speed was 1150 plus/minus 25 RPM; exhaust gas temperature 400 C. plus/minus 10 C.; engine load (MAP) was 33 plus/minus 4 kPa; and run at stoichiometry using closed loop control.

FIG. 6 sets forth the data illustrating the advantages of the sensors disclosed herein comprising an annealed catalyst containing protective coating. A graphical illustration of the same data is set forth in FIG. 7. The nearly horizontal long dash—short dash black line just above 1.004 lamba is the above described reference sensor. The dashed line beginning just below 1.002 lambda and ending at 1.01 is a competitor sensor. The cluster of solid black lines running substantially parallel to the reference line are the sensors disclosed herein. It will be appreciated that ideally, a sensor will have a constant lambda of 1.000 throughout the duration of the test. The sensors comprising the annealed catalyst as disclosed herein are advantageous for both their beginning and ending values below 1.004.

A Hot Rich Aging Test was also conducted on other sensors of the same test batch. This schedule exposed the oxygen sensors to an exhaust system environment which combined high temperature and a rich chemistry (unburned carbon monoxide, hydrogen, and hydrocarbons). The engine was a 2.3 liter Oldsmobile L-4 or equivalent; fuel system was the OEM Port Fuel Injection; fuel was unleaded regular gasoline; oil was SAE 30W, API SG or equivalent; oil consumption was a maximum of 2 quarts in 50 hours; automatic engine shutdown; 815 degree C. temperature; 6000 RPM engine speed; 110 degree C. engine coolant temperature; 130 degree C. engine oil temperature.

The engine speed is 2800 plus/minus 300 RPM; engine load was approximately 90 kPa, but minor adjustments (10%) were made to achieve the temperature of 800 C. plus/minus 10 C.

Figure 8:
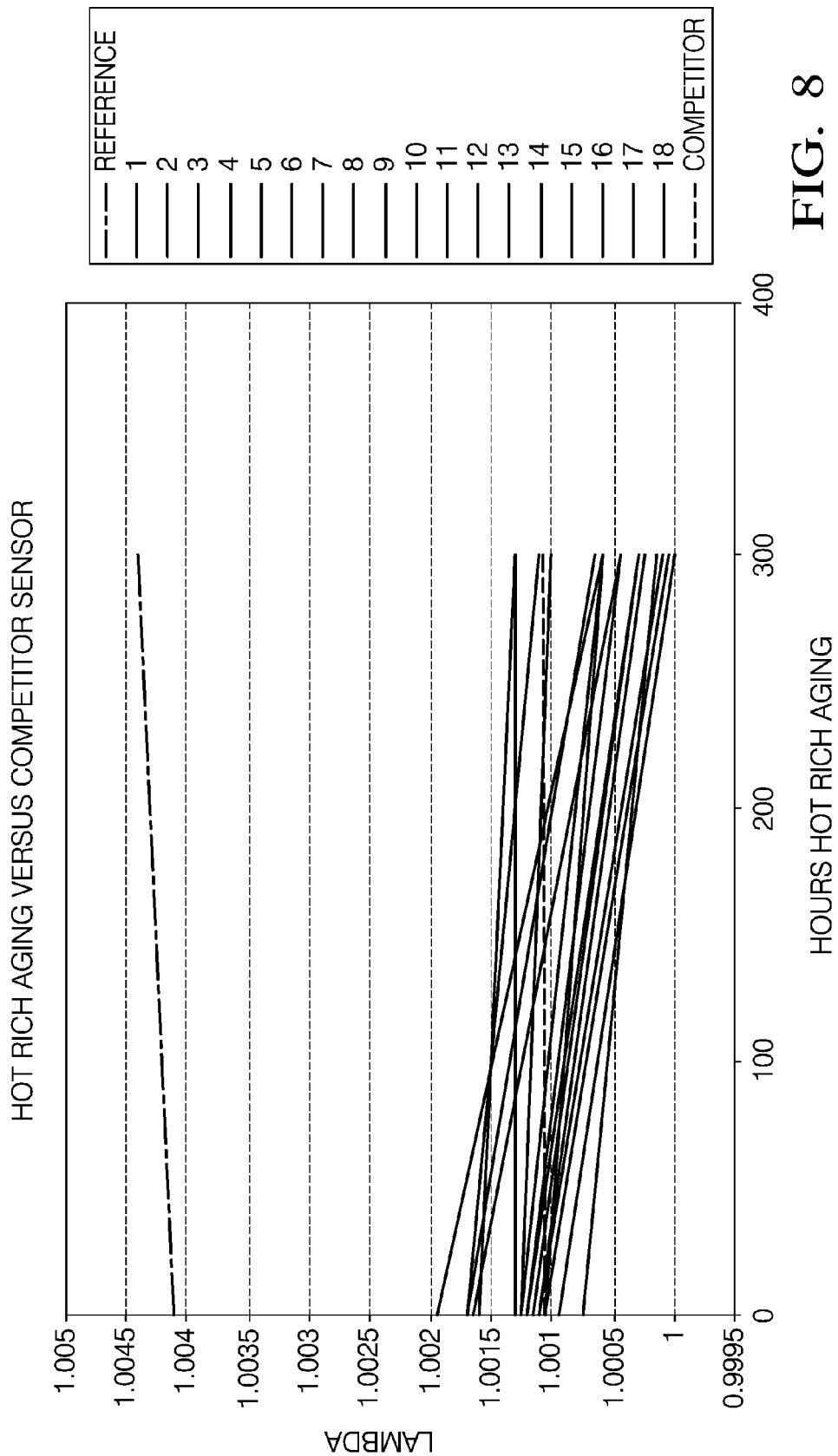
FIG. 8 is a graphical illustration comparing sensors comprising the disclosed annealed catalysts again a reference sensor and a competitive sensor in a Hot Rich Aging Test.

FIG. 9 sets forth the data illustrating the advantages of the sensors disclosed herein comprising an annealed catalyst containing protective coating. A graphical illustration of the same data is set forth in FIG. 8. In this case, the competitor sensor is represented by the dashed black line. The above described reference sensor is represented by the long dash—short dash black line. The cluster of solid black lines are the sensors disclosed herein. It will be appreciated that ideally, a sensor will have a constant lambda of 1.000 throughout the duration of the test.

The RAT (Rapid Aging Test) exposes oxygen sensors to a high temperature, thermally cycling, chemically poisoned engine exhaust stream environment.

The engine was a 2.3 liter Oldsmobile Quad-4 or equivalent; the engine control was OEM (Original Equipment Manufacturer) closed loop (port fuel injection); the fuel was unleaded regular gasoline; and the oil was Lubrizol OS163790. The engine shutdown was: test temperature was 925 C. plus/minus 5 C.; 6000 RPM engine speed; 110 C. engine coolant temperature; and 130 C. engine oil temperature. The sensors have 13.5 plus/minus 0.3V applied to the heaters.

(Step 1) Minimum temperature 250 C. plus/minus 25 C. reached at the end of 1.5 minutes; 1000 RPM plus/minus 300 RPM; Manifold Absolute Pressure (MAP) 40 plus/minus 10 kPa; Air/fuel ratio—run engine using OEM closed loop calibration, but sensors subjected to lean conditions by injecting air into the exhaust pipe.

The percentage of injected air (shop air at line pressure; injected ahead of the test oxygen sensors but behind the oxygen sensor controlling the engine) was as needed to meet the above temperature requirement. Total time at Step 1 was 1.5 minutes plus/minus 1 second.

(Step 2) Minimum temperature 400 plus/minus 50 C. reached at the the end of 5 minutes; engine speed 1000 plus/minus 300 RPM; engine load (MAP) was 35 plus/minus 10 kPa; air/fuel ratio—engine run using OEM closed loop calibration; total time this step was 5 minutes plus/minus 1 second. Ramp time from this step to next step was 10 seconds plus/minus 5 seconds. This ramp time was included in the total time for Step 3.

(Step 3) The Peak temperature was 800 plus/minus 50 C. reached at the end of 1.5 minutes; engine speed was 4200 plus/minus 200 RPM; engine load (MAP) was 90 plus/minus 5 kPa; air/fuel ratio was 12:1 to 13:1; total time at Step 3 was 1.5 minutes plus/minus 1 second. Step 3 to Step 4 ramp time is 10 seconds; this ramp time was included in the total time at Step 4.

(Step 4) Peak temperature 910 plus/minus 5 C. reached at the end of 10 minutes; Engine speed 3500 was plus/minus 200 RPM; engine load(MAP) was 70 plus/minus 5 kPa; air/fuel ratio—run engine using OEM closed loop calibration. Total time at Step 4: 10 minutes plus/minus 1 second. Step 4 to Step 1 ramp time: 10 seconds plus/minus 5 seconds. This ramp time was included in the total time at Step 1. Total combined test cycle time is 18 minutes plus/minus 4 seconds.

Oil consumption measurement was a follows: measured and recorded oil consumption every 50 hours; shut down the engine for 30-60 minutes before checking the oil using the OEM dipstick; oil added from a volumetric container (graduated cylinder or equivalent) until the level comes up to the full mark on the dipstick. Recorded the amount of oil added from the volumetric container.

Figure 10:
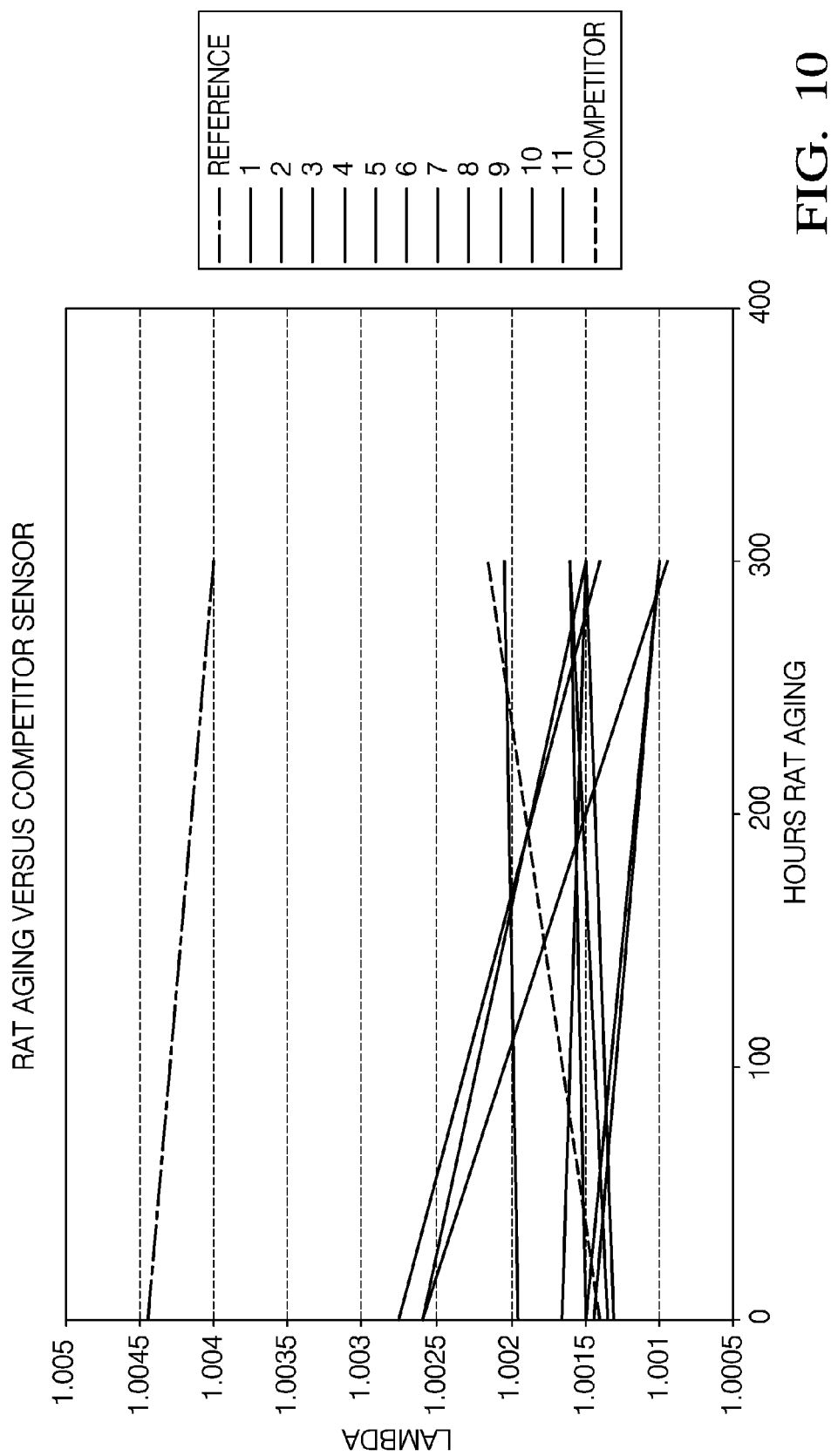
FIG. 10 is a graphical illustration comparing sensors comprising the disclosed annealed catalysts again a reference sensor and a competitive sensor in a RAT Aging Test.

FIGS. 10 and 11 respectively provide a graphical illustration of the test results and the test data itself. The reference sensor is illustrated by a long dash—short dash line while the competitor sensor is represented by the dashed black line. The cluster of solid black lines are the sensors disclosed herein. It will be appreciated that ideally, a sensor will have a constant lambda of 1.000 throughout the duration of the test.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the present application.

What is claimed is:

1. A sensor comprising:
   a sensing electrode having a first and second side and a first electrical lead in electrical communication with said sensing electrode;
   a reference electrode having a first and second side and a second electrical lead in electrical communication with said reference electrode;
   an electrolyte disposed between and in intimate contact with said first side of said sensing electrode and said first side of said reference electrode; and
   a first protective coating having a first and second side said first side disposed adjacent to said second side of said sensing electrode, said first coating formed by the process comprising the steps of:
   subjecting a mixture of a finely divided catalyst and a refractory metal oxide powder to a specific amount of thermal energy, the amount being either equal to or greater than that received from heating the metal catalyst for 24 hours at a temperature of 930 degrees C. for 24 hours in air but being no greater than that received from heating the metal catalyst for 24 hours at 1030 degrees C. in air, so as to produce an annealed catalyst having reduced catalytic activity relative to its catalytic activity before annealing;
   mixing the annealed catalyst with a first alumina slurry containing poison protective particles to provide an annealed catalyst slurry;
   applying the annealed catalyst slurry to said second side of said sensing electrode; and
   firing the applied annealed catalyst slurry at a temperature below the temperature used to anneal the catalyst by subjecting the applied annealed catalyst slurry to an amount of thermal energy being equal to or greater than that received by heating the applied annealed catalyst slurry to a temperature of 500 degrees C. for 1 hour but being no greater than that received from heating the applied annealed catalyst slurry to a temperature of 800 degrees C. for 4 hours.

2. The sensor of claim 1 wherein the annealed catalyst comprises at least one metal catalyst that has been subjected to an amount of thermal energy equal to being equal to that received from heating the metal catalyst for 24 hours at a temperature of 1005±25 degrees C. for 24 hours in air.

3. The sensor of claim 1, wherein said first coating is from 0.01 to 0.25 mm thick.

4. The sensor of claim 3, wherein said first coating is from 0.10 to 0.25 mm thick.

5. The sensor as in claim 1, further comprising a second protective coating having a first side disposed adjacent to said second side of said first protective coating.

6. The sensor as in claim 5, wherein said second coating is from 0.05 to 0.25 mm thick.

7. The sensor as in claim 6, wherein said second coating is from 0.05 to 0.10 mm thick.

8. The sensor of claim 5 wherein said second coating comprises the result of calcining an alumina slurry comprising at least 45 wt % of a high surface area alumina that is La stabilized.

9. The sensor as in claim 1, wherein the metal catalyst comprises platinum.

* * * * *